United States Patent [19]

Fitzgerald et al.

[11] Patent Number: 5,288,904

[45] Date of Patent: Feb. 22, 1994

[54] METHOD FOR THE DECOMPOSITION OF TRICHLOROACETIC ACID

[75] Inventors: Maurice Fitzgerald, Co. Wicklow; Eithne Cantwell, Co. Kildare, both of Ireland

[73] Assignee: Schering Corporation, Kenilworth, N.J.

[21] Appl. No.: 56,976

[22] Filed: May 4, 1993

[51] Int. Cl.$^5$ ............................................. C07C 53/02
[52] U.S. Cl. ..................................... 562/609; 562/513
[58] Field of Search ................ 562/607, 608, 609, 513

[56] References Cited

U.S. PATENT DOCUMENTS 4,612,389  9/1986  Gupton et al. ................ 562/609 X
4,898,644  2/1990  Van Horn ...................... 562/609 X

OTHER PUBLICATIONS

*Merck Index*, 11th Ed., p. 1515 (1989).
Verhock, *J. Amer. Chem. Soc.*, 56, 571–577 (1934).

*Primary Examiner*—Arthur C. Prescott
*Attorney, Agent, or Firm*—Paul A. Thompson; Edward H. Mazer

[57] ABSTRACT

A process for the decomposition of trichloroacetic acid (TCAA) to form chlorides, carbonates and formates is disclosed. The process comprises treating TCAA with 6 or more equivalents of a metal hydroxide at a temperature above 60° C.

7 Claims, No Drawings

METHOD FOR THE DECOMPOSITION OF TRICHLOROACETIC ACID

BACKGROUND OF THE INVENTION

Trichloroacetic acid (TCAA) is used in high concentration for the isolation and purification of protein, such as recombinant alpha-interferon, from fermentation mixtures during commercial production. Consequently, large quantities of TCAA are generated in the waste stream. TCAA is corrosive, is not biodegradable and requires disposal in an environmentally acceptable manner.

The *Merck Index*, 11th Ed., (1989) p. 1515, discloses the decomposition products of TCAA as being chloroform, HCl, carbon dioxide and carbon monoxide.

Methods for the chemical decomposition of TCAA are known. For example, Verhock, *J. Amer. Chem. Soc.*, 56, (1934) 571, describes a process for decomposing TCAA comprising heating various salts of TCAA at 70° C., to form chloroform, carbon dioxide and small amounts of HCl. This process is unsuitable for the commercial destruction of TCAA because the chloroform produced is a suspect carcinogen creating new handling and disposal problems.

SUMMARY OF THE INVENTION

The present invention involves a process for decomposing TCAA by treating with 6 or more equivalents of a metal hydroxide at a temperature above 60° C.

Preferred is a process wherein 6 or more equivalents of the metal hydroxide are used at a temperature of 90° to 150° C. Also preferred is a process wherein the metal hydroxide is selected from an alkali metal hydroxide, an alkaline earth hydroxide, or a combination thereof.

More preferred is a process wherein 6 or more equivalents of a metal hydroxide, wherein the metal hydroxide is selected from NaOH, KOH, or a mixture thereof, is used at a temperature of 90° to 120° C., preferably at 100° to 115° C.

DETAILED DESCRIPTION

As used herein the term "metal hydroxide" means an alkali metal hydroxide, an alkaline earth hydroxide, or a combination thereof;

"alkali metal hydroxide" means NaOH, KOH or LiOH; and

"alkaline earth hydroxide" means $Mg(OH)_2$ or $Ca(OH)_2$.

The process of the present invention comprises contacting the waste stream containing TCAA with an excess of a metal hydroxide at a temperature above 60° C. The TCAA and metal hydroxide can be combined at a temperature of above 60° C. Alternatively the TCAA and metal hydroxide can be combined at 60° C., or at a temperature below 60° C., then heated to a temperature in excess of 60° C. to carry out the decomposition.

The contacting is carried out in the presence of water. The metal hydroxide is introduced as an aqueous solution or alternatively as a solid. Similarly, the TCAA can be introduced as an aqueous solution or alternatively as a solid. Where both the TCAA and the metal hydroxide are introduced as a solid, water is also added.

The decomposition method of the present invention results in the chemical reaction of TCAA and the metal hydroxide to form the corresponding metal chloride, metal carbonate and metal formate. For example, where the metal hydroxide is NaOH the following chemical reaction takes place:

$$CCl_3COOH + 6NaOH \rightarrow 3NaCl + Na_2CO_3 + NaOC(O)H + 3H_2O$$

Where the metal hydroxide is a bivalent metal hydroxide, i.e., an alkaline earth metal hydroxide, 6 equivalents of hydroxide anion are provided by 3 mole of equivalents of the metal hydroxide. For example, where the metal hydroxide is $Ca(OH)_2$ the following chemical reaction takes place:

$$CCl_3COOH + 3\,Ca(OH)_2 \longrightarrow$$
$$3/2\,CaCl_2 + CaCO_3 + 1/2\,Ca[OC(O)H]_2 + 3\,H_2O$$

The TCAA decomposition method of the present invention has significant advantages over the prior art methods described above. The process of the present invention results in the decomposition of TCAA to form chlorides, carbonates and formates which are readily disposed of.

The decomposition of TCAA during the process of the present invention is monitored by liquid chromatography as follows:

---

Column: Nucleosil ® 120.5, C-18, 250 × 4.6 mm;
Mobile phase: 0.02 M $KH_2PO_4$ (aqueous), adjusted to pH = 2 with $H_3PO_4$, at a flow rate of 1.8 mL/min.
Detector: UV absorbance at 200 nm, or refractive index at 35° C.

---

The disappearance of TCAA and the formation of formate anion are both followed using this methodology.

The presence and quantity of chloride anion formed by the decomposition of TCAA is determined by titration using $AgNO_3$.

The presence and quantity of carbonate anion formed by the decomposition of TCAA is determined by titration with HCl using phenolthalein (pH=8 to 10) and methyl orange (pH=3.2 to 4.4) to indicate the two endpoints for carbonate anion.

The following examples are illustrative of the process of the present invention:

EXAMPLE 1

Combine 163.5 g (1 mole) of trichloroacetic acid (TCAA), 500 mL of water and 600 mL of 10N NaOH (aqueous) and heat the mixture at 90°-100° C. Monitor the decomposition of TCAA by liquid chromatography as described above. The decomposition of TCAA is complete in approximately 3 hours as indicated by the absence of TCAA and the presence of 1 mole of formate anion in the resulting mixture. Titration via the methods described above confirms the presence of 3 moles of chloride and 1 mole of carbonate.

Using substantially the same procedure, the decomposition of TCAA can be accomplished using 240 g (6 moles) of NaOH pellets in place of the 10N NaOH solution.

EXAMPLE 2

Following the procedure of Example 1, TCAA is decomposed by heating with 6 equivalents of KOH, or 6 equivalents of a mixture of KOH and NaOH.

EXAMPLE 3

The process of Example 1 is carried out using less than 6 equivalents of NaOH. The decomposition products include chloroform and carbon monoxide.

EXAMPLE 4

The process of Example 1 is carried out at a temperature of 60° C. The reaction progresses very slowly as determined by liquid chromatography.

We claim:

1. A process for decomposing trichloroacetic acid comprising treating with 6 or more equivalents of a metal hydroxide at a temperature above 60° C.
2. The process of claim 1 wherein the temperature is 90° to 150° C.
3. The process of claim 1 wherein the metal hydroxide is selected from an alkali metal hydroxide, an alkaline earth hydroxide, or a combination thereof.
4. The process of claim 2 wherein the temperature is 90° to 120° C.
5. The process of claim 3 wherein the the metal hydroxide is selected from NaOH, KOH, or a mixture thereof.
6. The process of claim 5 wherein the temperature is 90° to 150° C.
7. The process of claim 6 wherein the temperature is 100° C. to 115° C.

* * * * *